(12) United States Patent
Osakabe et al.

(10) Patent No.: US 10,436,723 B2
(45) Date of Patent: Oct. 8, 2019

(54) X-RAY DIFFRACTOMETER WITH MULTILAYER REFLECTION-TYPE MONOCHROMATOR

(71) Applicant: RIGAKU CORPORATION, Akishima-shi, Tokyo (JP)

(72) Inventors: Takeshi Osakabe, Tokyo (JP); Tetsuya Ozawa, Tokyo (JP); Kazuhiko Omote, Tokyo (JP); Licai Jiang, Auburn Hills, MI (US); Boris Verman, Auburn Hills, MI (US); Yuriy Platonov, Auburn Hills, MI (US)

(73) Assignee: RIGAKU CORPORATION, Tokyo (JP)

( * ) Notice: Subject to any disclaimer, the term of this patent is extended or adjusted under 35 U.S.C. 154(b) by 349 days.

(21) Appl. No.: 15/312,881

(22) PCT Filed: Jan. 14, 2015

(86) PCT No.: PCT/JP2015/050717
§ 371 (c)(1),
(2) Date: Nov. 21, 2016

(87) PCT Pub. No.: WO2015/186369
PCT Pub. Date: Dec. 10, 2015

(65) Prior Publication Data
US 2017/0191950 A1    Jul. 6, 2017

(30) Foreign Application Priority Data
Jun. 5, 2014 (JP) .................................. 2014-116488

(51) Int. Cl.
*G01N 23/20008* (2018.01)
*G21K 1/04* (2006.01)
(Continued)

(52) U.S. Cl.
CPC ....... *G01N 23/20008* (2013.01); *G02B 7/003* (2013.01); *G02B 27/0977* (2013.01);
(Continued)

(58) Field of Classification Search
CPC ............ G21K 1/00; G21K 1/02; G21K 1/025; G21K 1/04; G21K 1/06; G21K 1/062;
(Continued)

(56) References Cited

U.S. PATENT DOCUMENTS

| 5,757,882 A | 5/1998 | Gutman |
| 6,041,099 A * | 3/2000 | Gutman ................. B82Y 10/00 378/84 |

(Continued)

FOREIGN PATENT DOCUMENTS

| DE | 198 33 524 A1 | 2/2000 |
| EP | 1 653 226 A1 | 5/2006 |

(Continued)

OTHER PUBLICATIONS

International Search Report dated Apr. 7, 2015, issued in counterpart application No. PCT/JP2015/050717. (2 pages).

(Continued)

*Primary Examiner* — Anastasia Midkiff
(74) *Attorney, Agent, or Firm* — Westerman, Hattori, Daniels & Adrian, LLP

(57) ABSTRACT

Only X-rays having a specific wavelength, selected from a group of focusing X-rays diffracted from a sample, are reflected from a monochromator based on a Bragg's condition, passed through a receiving slit and detected by an X-ray detector. The monochromator is configured to be freely removable, and arranged between the sample and a focal point at which the wavelength-selected focusing X-rays diffracted from the sample are directly focused. At this time, the monochromator is moved so as to position the (Continued)

monochromator as close to the focal point as possible. The monochromator comprises a multilayer mirror having an internal interplanar spacing, wherein said internal interplanar spacing varies continuously from one end of the monochromator to the other end.

12 Claims, 13 Drawing Sheets

(51) Int. Cl.
    *G21K 1/06*     (2006.01)
    *G02B 7/00*     (2006.01)
    *G02B 27/42*     (2006.01)
    *G02B 27/09*     (2006.01)
    *G01N 23/207*     (2018.01)

(52) U.S. Cl.
CPC ........... *G02B 27/4272* (2013.01); *G21K 1/04* (2013.01); *G21K 1/06* (2013.01); *G21K 1/062* (2013.01); *G01N 23/207* (2013.01); *G01N 2223/056* (2013.01); *G01N 2223/302* (2013.01); *G01N 2223/315* (2013.01); *G01N 2223/32* (2013.01); *G21K 2201/067* (2013.01)

(58) Field of Classification Search
CPC .. G21K 1/10; G21K 2201/00; G21K 2201/06; G21K 2201/061; G21K 2201/067; G02B 5/00; G02B 5/005; G02B 5/18; G02B 5/1814; G02B 5/1828; G02B 5/1838; G02B 5/1861; G02B 7/00; G02B 7/003–5; G02B 7/18; G02B 7/182; G02B 27/0938; G02B 27/0944; G02B 27/0977; G02B 27/0988; G02B 27/0012; G02B 27/0037; G02B 27/1086; G02B 27/14; G02B 27/16; G02B 27/30; G02B 27/42; G02B 27/4205; G02B 27/4216; G02B 27/4272; G02B 27/4277; G01N 23/00; G01N 23/20; G01N 23/20008; G01N 23/20058; G01N 23/205; G01N 23/2055; G01N 23/207; G01N 23/2076; G01N 2223/00; G01N 2223/05; G01N 2223/052; G01N 2223/055; G01N 2223/056; G01N 2223/0561; G01N 2223/0566; G01N 2223/0568; G01N 2223/30; G01N 2223/302; G01N 2223/315–317; G01N 2223/32; G01N 2223/33; G01N 2223/3301; G01N 2223/50; G01N 2223/501

See application file for complete search history.

(56) References Cited

U.S. PATENT DOCUMENTS

| | | | |
|---|---|---|---|
| 6,226,349 | B1 | 5/2001 | Schuster et al. |
| 2004/0190681 | A1* | 9/2004 | Omote ................... G01N 23/20 378/71 |
| 2007/0003012 | A1 | 1/2007 | Taguchi et al. |
| 2009/0086910 | A1 | 4/2009 | Ozawa et al. |
| 2010/0086104 | A1* | 4/2010 | Michaelsen ............. G21K 1/04 378/71 |
| 2011/0085644 | A1* | 4/2011 | Verman .................. B82Y 10/00 378/147 |
| 2013/0259200 | A1* | 10/2013 | Omote ................. G01N 23/207 378/74 |

FOREIGN PATENT DOCUMENTS

| | | |
|---|---|---|
| JP | 4-178547 A | 6/1992 |
| JP | 8-47491 A | 2/1996 |
| JP | 9-218170 A | 8/1997 |
| JP | 2716949 B2 | 2/1998 |
| JP | 2000-502188 A | 2/2000 |
| JP | 2007-10455 A | 1/2007 |
| JP | 2007-10486 A | 1/2007 |

OTHER PUBLICATIONS

Extended European Search Report dated Nov. 17, 2017, issued in counterpart European Application No. 15802969.4. (10 pages).

* cited by examiner

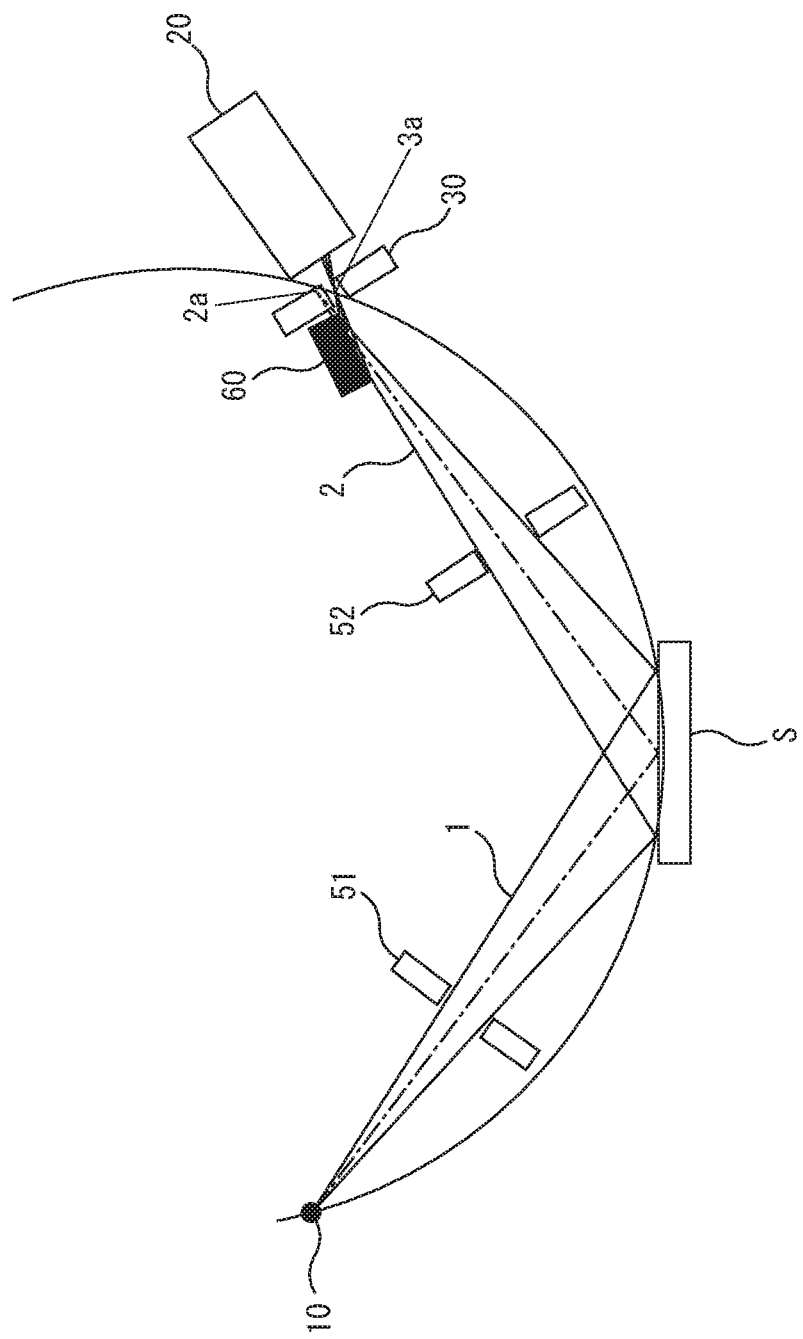

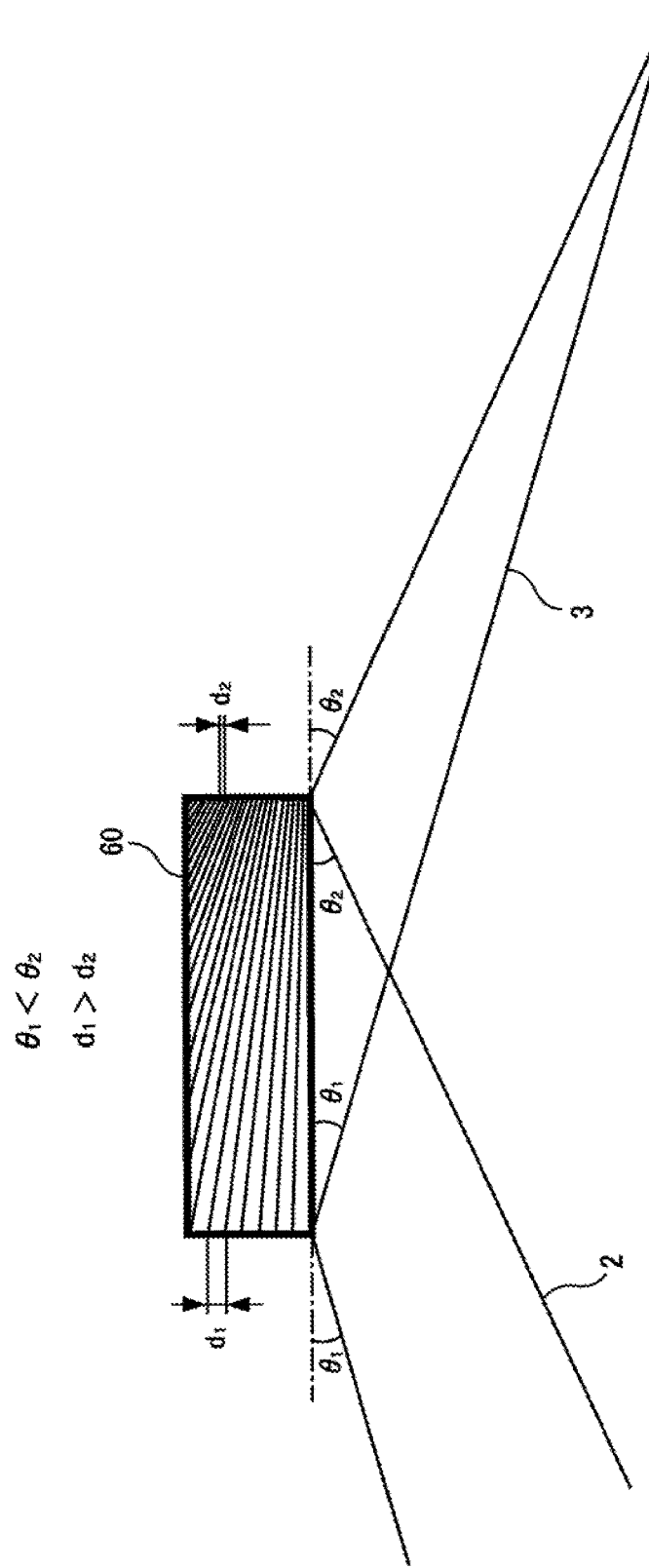

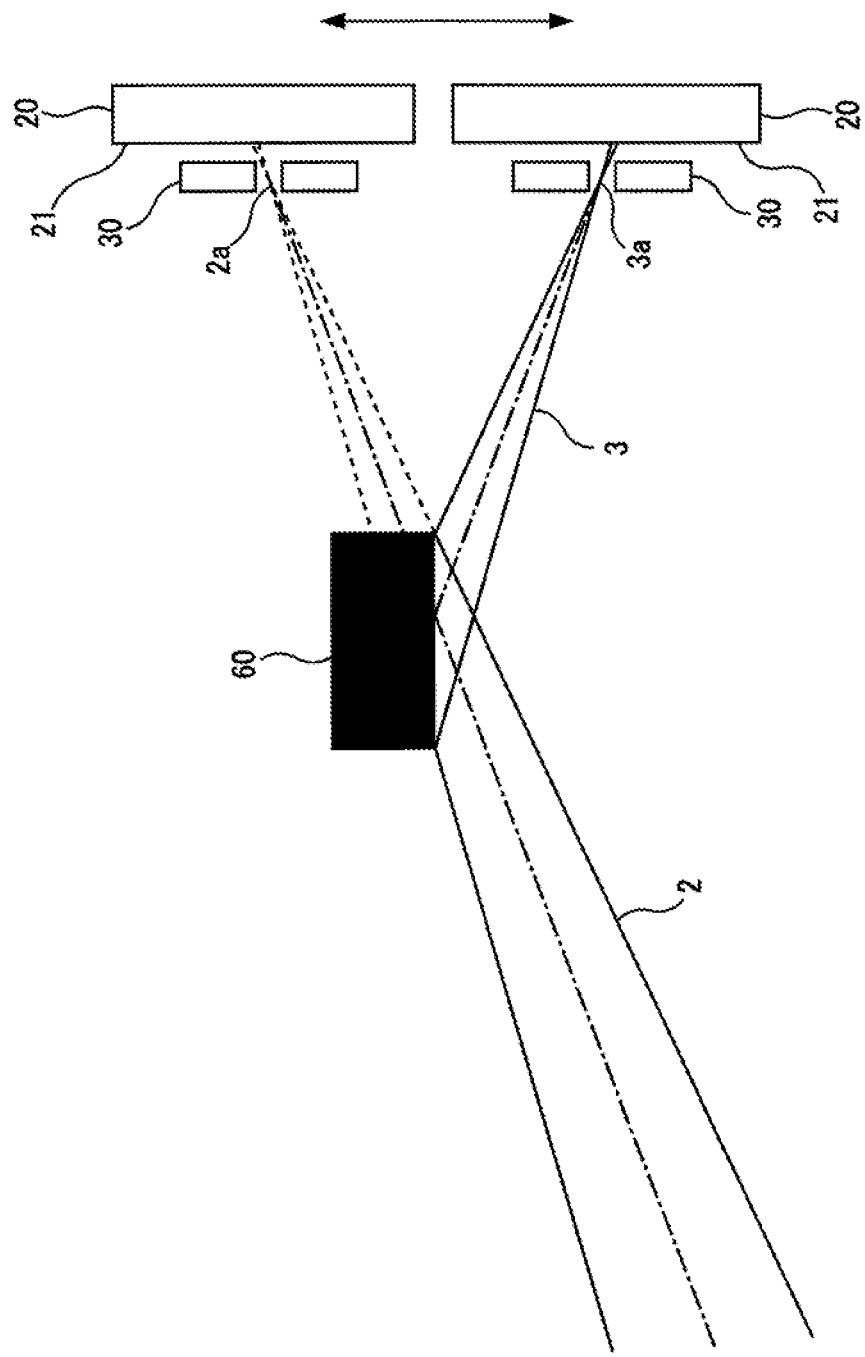

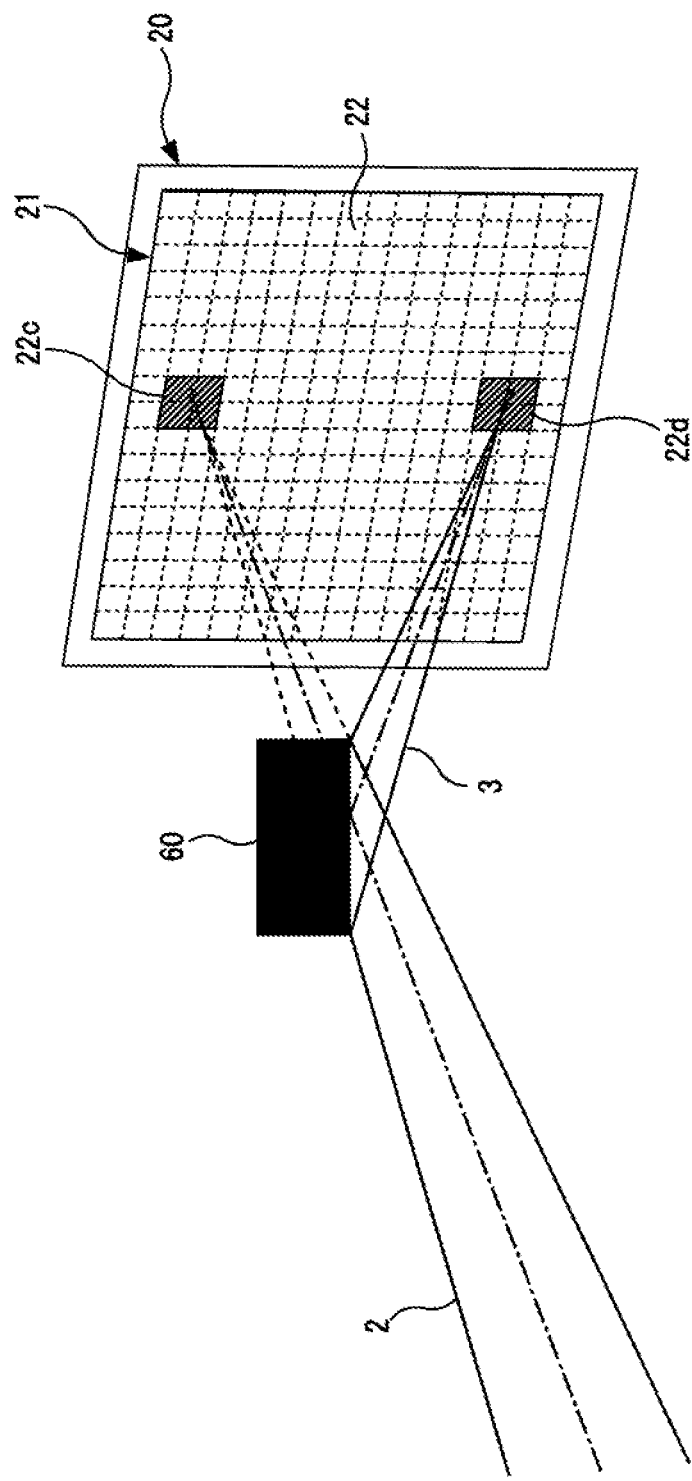

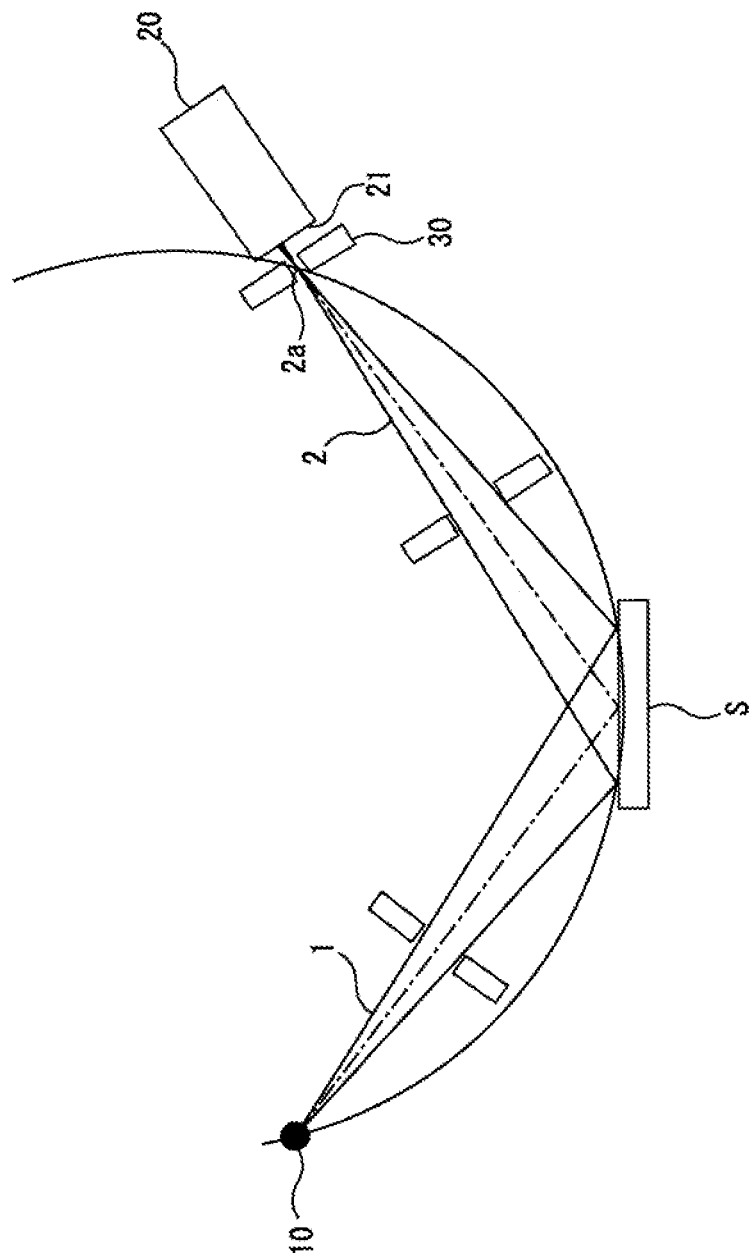

X-RAY DIFFRACTOMETER WITH MULTILAYER REFLECTION-TYPE MONOCHROMATOR

TECHNICAL FIELD

The present invention relates to an X-ray diffractometer for detecting X-rays diffracted from a sample when the sample is irradiated with X-rays, and particularly to an X-ray diffractometer constituting an X-ray optical system in which X-rays diffracted from a sample are focusing X-rays focused on one point.

BACKGROUND ART

An X-ray diffractometer is known as one of apparatuses for analyzing crystallinity, crystal structures, etc. of samples.

FIG. 10 is a schematic diagram showing an exemplary arrangement of an X-ray optical system in a conventional X-ray diffractometer.

As shown in FIG. 10, the X-ray optical system is configured so that the surface of a sample S disposed on a sample stage is irradiated with X-rays generated in an X-ray source 10, and X-rays diffracted from the sample S are detected by an X-ray detector 20. As not shown in FIG. 10, the setting of an X-ray irradiation angle to the surface of the sample S and the movement of the X-ray detector 20 in a direction along which the X-rays diffracted from the sample S are captured are performed by operating a goniometer or the like.

The illustrated X-ray optical system is called as a Bragg-Brentano optical system in which a sample is irradiated with divergent X-rays 1 diverging radially from the X-ray source 10, and focusing X-rays 2 focused on one point are diffracted from the sample S.

The X-ray detector 20 is arranged at the focal point 2a (or a rear position approximate to the focal point) of the focusing X-rays 2 diffracted from the sample S.

A receiving slit 30 is arranged in front of an X-ray detection face 21 of the X-ray detector 20. The receiving slit 30 is an optical component for adjusting the cross-sectional area of X-rays to be guided to the X-ray detector 20 to adjust the resolution of the X-ray detector 20.

FIG. 11 is a schematic diagram showing an exemplary arrangement of the X-ray optical system in which an optical component called as a monochromator 40 on the optical path of the focusing X-rays 2 diffracted from the sample in the conventional X-ray diffractometer described above.

The focusing X-rays 2 diffracted from the sample S contain continuous X-rays having a wavelength distribution and plural characteristic X-rays. The monochromator 40 is an optical component having a function of extracting only X-rays having a specific wavelength (for example, $K\alpha 1$ ray or $K\alpha 2$ ray) from the focusing X-rays 2 to monochromate the focusing X-rays 2. The arrangement of the monochromator 40 on the optical path of the focusing X-rays 2 diffracted from the sample S makes it possible to remove noise components and detect only diffracted X-rays having a specific wavelength required for a sample analysis, so that the detection precision of the X-ray detector 20 (the detection precision of the diffraction angle) can be enhanced.

As shown in FIG. 11, the conventional X-ray diffractometer is configured so that the monochromator 40 is arranged behind the receiving slit 30, diffracted X-rays which focus at the focal point 2a and then diverge are made to enter the monochromator 40, and then monochromated diffracted X-rays are reflected. The diffracted X-rays which are reflected from the surface of the monochromator 40 focus at a second focal point 2c as focusing X-rays again. The X-ray detection face 21 of the X-ray detector 20 is arranged at the second focal point 2c (or a rear position approximate to the second focal point 2c).

For example, Patent Document 1 discloses a conventional X-ray diffractometer having this type of X-ray optical system.

PRIOR ART DOCUMENTS

Patent Documents

Patent Document 1: JP-H04-178547 (U.S. Pat. No. 2,866,471)
Patent Document 2: FIG. 2 of U.S. Pat. No. 5,757,882
Patent Document 3: JP-2007-10486

DISCLOSURE OF THE INVENTION

Problem to be Solved by the Invention

As described above, in the conventional X-ray optical system, the monochromator 40 is arranged at the rear side of the second focal point 2a of the focusing X-rays 2 diffracted from the sample S, and the X-rays reflected from the monochromator 40 are detected by the X-ray detector 20. Therefore, the conventional X-ray optical system has a problem that the optical path length of the diffracted X-rays until the X-rays reach the X-ray detector 20 is further increased, resulting in attenuation of the intensity of the diffracted X-rays.

The present invention has been implemented in view of the foregoing situation, and has an object to provide an X-ray diffractometer that can monochromate focusing X-rays diffracted from a sample by a monochromator without increasing the optical path length of the focusing X-rays until the focusing X-rays reach an X-ray detector.

Means of Solving the Problem

An X-ray diffractometer according to the present invention is characterized by comprising: an X-ray source for irradiating a sample with X-rays; a reflection type monochromator for receiving focusing X-rays diffracted from a sample and reflecting only focusing X-rays having a specific wavelength based on a Bragg's condition; an X-ray detector for detecting focusing X-rays monochromated by the monochromator; and a unit that adjusts measurement resolution of the X-ray detector, wherein the monochromator is arranged on an X-ray optical path between a focal point at which the focusing X-rays from the sample are directly focused and the sample.

Since the monochromator is arranged in front of the focal point at which the focusing X-rays from the sample focus, the optical path length of the focusing X-rays passing from the sample through the monochromator to the X-ray detector is shorter as compared with a case where the monochromator is arranged behind the focal point at which the focusing X-rays from the sample focus. In the X-ray detector, the X-ray detection face is arranged at (or proximately behind) the focal point of focusing X-rays reflected from the monochromator.

Here, it is preferable that the monochromator comprises a multilayer mirror having an internal interplanar spacing that varies continuously from one end to the other end.

Furthermore, it is preferable that the multilayer mirror is configured so as to adjust the interplanar spacing so that a interplanar spacing $d_1$ in a depth direction at a site to which the focusing X-rays are incident at an incident angle $\theta_1$ and a interplanar spacing $d_2$ in the depth direction at a site to which the focusing X-rays are incident at an incident angle $\theta_2$ satisfy the following equation based on the Bragg's condition: $2d_1 \times \sin\theta_1 = 2d_2 \times \sin\theta_2 = n\lambda$, wherein $\lambda$ represents the wavelength of the diffracted X-rays, and n represents an integer.

By applying the thus-configured multilayer mirror to the monochromator, only X-rays having a specific wavelength can be reflected and extracted over the whole width of focusing X-rays which are incident to the surface of the monochromator at different angles.

The incident face of the above monochromator for the focusing X-rays can be configured as a flat surface, whereby the monochromator can be easily manufactured. However, the present invention is not limited to this, and the incident face of the focusing X-rays may be configured as a curved surface as occasion demands.

Furthermore, it is preferable that the monochromator is arranged in proximity to a focal point at which the focusing X-rays diffracted from the sample are directly focused to the extent that the monochromator does not interfere with the X-ray detector.

The arrangement of the monochromator at the position described above enables the focal point of the focusing X-rays reflected from the monochromator to be close to the focal point at which the focusing X-rays diffracted from the sample are directly focused.

The unit that adjusts the measurement resolution of the X-ray detector may be configured by a receiving slit, for example. The receiving slit is arranged in front of the X-ray detection face of the X-ray detector.

Furthermore, a two-dimensional X-ray detector capable of two-dimensionally detecting X-rays incident to the X-ray detection face is applicable as the X-ray detector.

The two-dimensional X-ray detector is preferably configured to have a two-dimensional X-ray detection function capable of two-dimensionally detecting X-rays incident to the X-ray detection face, a one-dimensional X-ray detection function capable of one-dimensionally detecting X-rays incident to the X-ray detection face and a zero-dimensional X-ray detection function capable of zero-dimensionally detecting X-rays incident to the X-ray detection face, the two-dimensional X-ray detection function, the one-dimensional X-ray detection function and the zero-dimensional X-ray detection function being switchable to one another.

By using the two-dimensional X-ray detector having the functions as described above, the two-dimensional X-ray detection, the one-dimensional X-ray detection and the zero-dimensional X-ray detection can be performed by a single two-dimensional X-ray detector, and the degree of freedom of measurements can be increased.

Here, the zero-dimensional X-ray detection means that only the intensity of X-rays is detected, the one-dimensional X-ray detection means that the intensity of X-rays and one-dimensional position information thereof is detected, and further the two-dimensional X-ray detection means that the intensity of X-rays and two-dimensional position information are detected.

The X-ray diffractometer of the present invention is configured so that the monochromator is removable from the optical path of the focusing X-rays diffracted from the sample.

Here, the X-ray detection face of the X-ray detector has an area that allows detection of focusing X-rays diffracted from the sample in an X-ray optical system in which the monochromator is removed from the optical path of the focusing X-rays and detection of focusing X-rays that are diffracted from the sample and reflected from the monochromator in an X-ray optical system in which the monochromator is arranged on the optical path of the focusing X-rays.

The above configuration can be easily implemented by arranging the monochromator in proximity to a focal point at which the focusing X-rays diffracted from the sample are directly focused to the extent that the monochromator does not interfere with the X-ray detector. By arranging the monochromator as described above, the focal point of the focusing X-rays reflected from the monochromator can be approached to the focal point of the focusing X-rays diffracted from the sample when the monochromator is removed.

The receiving slit is configured to be freely positionally changeable between a position through which the focusing X-rays diffracted from the sample pass in the X-ray optical system in which the monochromator is removed from the optical path of the focusing X-rays, and a position through which the focusing X-rays diffracted from the sample and reflected from the monochromator passes in the X-ray optical system in which the monochromator is arranged on the optical path of the focusing X-rays.

This configuration can implement, without movement of the X-ray detector, both of the X-ray optical system in which the monochromator is removed from the optical path of the focused X-rays and the X-ray optical system in which the monochromator is arranged on the optical path of the focused X-rays.

In the configuration that the monochromator is removed from the optical path of focused X-rays diffracted from the sample, the X-ray detector can be configured as follows. That is, the X-ray detector may be configured to be freely positionally changeable between a detection position of the focusing X-rays diffracted from the sample and passing through the receiving slit in the X-ray optical system in which the monochromator is removed from the optical path of the focusing X-rays, and a detection position of the focusing X-rays diffracted from the sample, reflected from the monochromator and passing through the receiving slit in the X-ray optical system in which the monochromator is arranged on the optical path of the focusing X-rays.

The X-ray diffractometer of this invention may be configured as follows.

The monochromator may be configured to be removable from the optical path of the focusing X-rays diffracted from the sample.

A two-dimensional X-ray detector capable of two-dimensionally detecting X-rays incident to the X-ray detection face may be applied as the X-ray detector.

The X-ray detection face of the X-ray detector has an area that allows detection of focusing X-rays diffracted from the sample in an X-ray optical system in which the monochromator is removable from the optical path of the focusing X-rays and detection of focusing X-rays that are diffracted from the sample and reflected from the monochromator in an X-ray optical system in which the monochromator is arranged on the optical path of the focusing X-rays.

This configuration can be easily implemented by arranging the monochromator in proximity to the focal point at which the focusing X-rays diffracted from the sample are directly focused to the extent that the monochromator does not interfere with the X-ray detector as described above.

Furthermore, the X-ray detector has a function of freely changing an X-ray detection area between a first X-ray detection area for detecting focusing X-rays diffracted from the sample in the X-ray optical system in which the monochromator is removable from the optical path of the focusing X-rays, and a second X-ray detection area for detecting focusing X-rays diffracted from the sample and reflected from the monochromator in the X-ray optical system in which the monochromator is arranged on the optical path of the focusing X-rays.

Here, the function of freely changing the X-ray detection area in the X-ray detector constitutes a unit that adjusts the measurement resolution of the X-ray detector. Accordingly, the receiving slit described above is unnecessary.

In this configuration, it is preferable that the X-ray detector (two-dimensional X-ray detector) is configured to have a two-dimensional X-ray detection function capable of two-dimensionally detecting X-rays incident to the X-ray detection face, a one-dimensional X-ray detection function capable of one-dimensionally detecting X-rays incident to the X-ray detection face and a zero-dimensional X-ray detection function capable of zero-dimensionally detecting X-rays incident to the X-ray detection face, the two-dimensional X-ray detection function, the one-dimensional X-ray detection function and the zero-dimensional X-ray detection function being switchable to one another. By using the two-dimensional X-ray detector having the functions described above, the two-dimensional, one-dimensional and zero-dimensional X-ray detection can be performed by a single two-dimensional X-ray detector, and the degree of freedom of measurements can be increased.

As described above, according to the present invention, there can be provided an X-ray diffractometer in which focusing X-rays diffracted from a sample can be monochromated by a monochromator without greatly increasing the optical path length of the focusing X-rays diffracted from the sample to the X-ray detector.

BRIEF DESCRIPTION OF THE DRAWINGS

FIG. 1 is a schematic diagram showing an exemplary structure of an X-ray diffractometer according to a first embodiment of the present invention.

FIG. 2 is a schematic diagram showing the configuration of a monochromator used in the first embodiment of the present invention.

FIG. 7 is a schematic diagram showing a main part of a X-ray diffractometer according to a second embodiment of the present invention.

FIG. 8 is a schematic diagram showing a main part of an X-ray diffractometer according to a third embodiment of the present invention.

FIG. 10 is a schematic diagram showing an exemplary arrangement of an X-ray optical system of a conventional X-ray diffractometer in which no monochromator is arranged.

DESCRIPTION OF REFERENCE NUMERALS

Figure 3A:
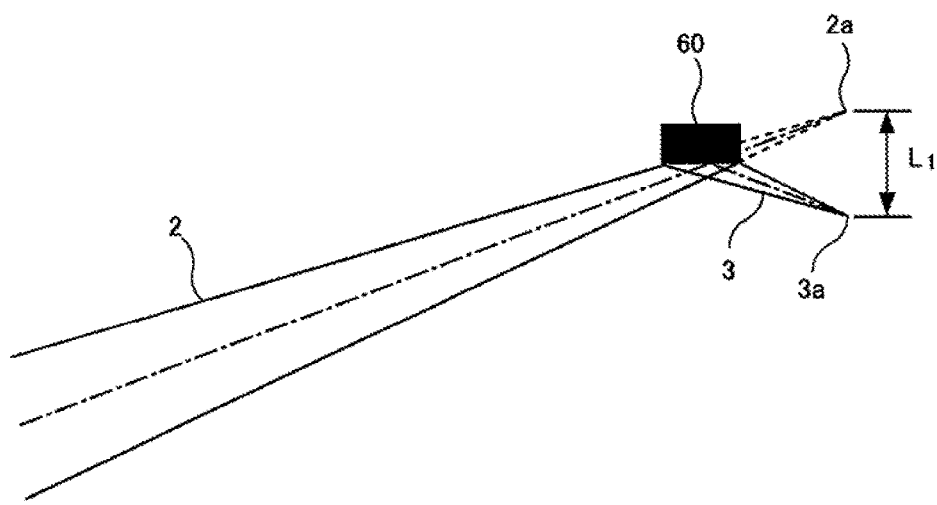
FIGS. 3A and 3B are diagrams showing the relationship between installation/removal of the monochromator and the positional variation of a focal point on which focusing X-rays are focused.

S: sample
10: X-ray source
20: X-ray detector,
21: X-ray detection face,
22: detection element
30: receiving slit
40, 60: monochromator
51: divergence slit,
52: scattering slit

BEST MODE FOR CARRYING OUT THE INVENTION

An embodiment of the present invention will be described hereunder in detail with reference to the drawings.

First Embodiment

First, an X-ray diffractometer according to a first embodiment of the present invention will be described with reference to FIGS. 1 to 6B and FIG. 10.

FIG. 1 is a schematic diagram showing an exemplary structure of the X-ray diffractometer according to the embodiment.

The X-ray diffractometer shown in FIG. 1 has an X-ray source 10, a divergence slit 51, a scattering slit 52, a monochromator 60, a receiving slit 30 and an X-ray detector 20, and is configured so that the surface of a sample S disposed on a sample stage is irradiated with divergent X-rays 1 occurring in the X-ray source 10, and focusing X-rays 2 diffracted from the sample S are monochromated by the monochromator 60 and made to enter the X-ray detector 20.

Here, the divergent X-rays 1 which diverge radially are emitted from the X-ray source 10. The divergent X-rays 1 emitted from the X-ray source 10 are restricted from spreading (divergent angle) by the divergence slit 51, and applied to the surface of the sample S. X-rays are diffracted from the sample S based on the Bragg's law. The diffracted X-rays from the sample S are focusing X-rays 2 focused on one point.

The X-ray diffractometer according to the embodiment shown in FIG. 1 is configured by adding a reflection type monochromator 60 to the conventional Bragg-Brentano type X-ray diffractometer shown in FIG. 10. The reflection type monochromator 60 has a function of reflecting only X-rays having a specific wavelength based on a Bragg's condition.

The monochromator 60 is arranged between the sample S and a focal point 2a (see FIG. 10) at which the focusing X-rays 2 from the sample S are directly focused.

The focusing X-rays 2 diffracted from the sample S are reflected and monochromated by the monochromator 60. That is, only focusing X-rays 2 having a specific wavelength (for example, Kα1 ray or Kα2 ray) out of the focusing X-rays 2 incident to the monochromator 60 are reflected from the monochromator 60 based on the Bragg's condition. As described above, the focusing X-rays 3 monochromated by the monochromator 60 are incident to the X-ray detection face 21 of the X-ray detector 20, and detected by the X-ray detector 20.

In this embodiment, the receiving slit 30 is arranged in front of the X-ray detection face 21 of the X-ray detector 20. As described above, the receiving slit 30 is an optical component which adjusts the cross-sectional area of X-rays to be guided to the X-ray detector 20 to adjust the resolution of the X-ray detector 20.

The setting of the X-ray irradiation angle to the surface of the sample S and the movement of the X-ray detector 20 in a direction along which the X-rays diffracted from the sample S are captured are performed by operating a goniometer or the like, which is not shown in FIG. 1. Furthermore, it is needless to say that an optical component for an X-ray diffractometer other than the exemplary structure shown in FIG. 1 may be mounted as occasion demands.

FIG. 2 is a schematic diagram showing the configuration of the monochromator 60 used in this embodiment.

In the monochromator 60 used in this embodiment, the incident face (surface) of the focusing X-rays 2 is configured as a flat surface. With respect to the inside of the monochromator 60, multiple lattice planes for diffracting X-rays having a specific wavelength(s) are formed to be layered by an artificial multilayer. The interval between the respective lattice planes is adjusted to continuously vary from one end of the monochromator 60 (the left end in FIG. 2) to the other end of the monochromator 60 (the right end in FIG. 2).

Here, it is assumed that the focusing X-rays 2 from the sample S are incident to the surface of one end portion (left end portion in FIG. 2) of the monochromator 60 at an incident angle $\theta_1$ as shown in FIG. 2. The interplanar spacing in the depth direction at the one end portion is represented by $d_1$. Furthermore, the focusing X-rays 2 from the sample S are incident to the surface of the other end portion (right end portion in FIG. 2) of the monochromator 60 at an incident angle $\theta_2$. The interplanar spacing in the depth direction at the other end portion is represented by $d_2$.

The interval of the respective lattice planes which are formed to be layered in the monochromator 60 varies continuously so as to satisfy the following equation based on the Bragg's condition: $2d_1 \times \sin\theta_1 = 2d_2 \times \sin\theta_2 = n\lambda$, wherein $\lambda$ represents the wavelength of the diffracted X-rays, and n represents an integer.

Accordingly, X-rays having a specific wavelength $\lambda$ are reflected at an angle of $\theta_1$ from the surface of the one end portion (the left end portion in FIG. 2) and also reflected at an angle of $\theta_2$ from the surface of the other end portion (the right end portion in FIG. 2). That is, the reflection type monochromator 60 having the configuration described above has a function of reflecting only X-rays having a specific wavelength out of incident focusing X-rays 2 at the same angle as the incident angle from the surface thereof, and focuses the X-rays as focusing X-rays 3 on one point.

The monochromator having this kind of function is publicly known, and it is disclosed in the U.S. Patent of the Patent Document 2, for example.

In the X-ray diffractometer according to this embodiment, the monochromator 60 is arranged to be freely removable from the optical path of the focusing X-rays 2. The monochromator 60 is arranged on the optical path of the focusing X-rays 2 to configure the X-ray optical system as shown in FIG. 1, whereas the monochromator 60 is removed from the optical path of the focusing X-rays 2 to configure the X-ray optical system as shown in FIG. 10.

The X-ray optical system of FIG. 1 in which the monochromator 60 is arranged on the optical path of the focusing X-rays 2 is capable of removing noise components with the monochromator 60, and enables only diffracted X-rays having a specific wavelength required for analysis of a sample S to be incident to the X-ray detector 20, so that the detection precision (the detection precision of the diffraction angle) of the X-ray detector 20 can be enhanced.

On the other hand, when the monochromator 60 is arranged on the optical path of the focusing X-rays 2, the intensity of the diffracted X-rays incident to the X-ray detector 20 is reduced. Therefore, for measurements, etc. which place more importance on the X-ray intensity than the diffraction angle, the X-ray optical system of FIG. 10 in which the monochromator 60 is removed from the optical path of the focusing X-rays 2 may be preferable.

In this embodiment, the monochromator 60 can be freely installed and removed, and it can be selected according to a measurement purpose which one of the enhancement of the detection precision and the increase of the X-ray intensity takes priority.

In connection with the free installation/removal configuration of the monochromator 60, the monochromator 60, the X-ray detector 20 and the receiving slit 30 of the X-ray diffractometer of this embodiment are configured as follows.

First, the monochromator 60 is arranged in proximity to a focal point at which focusing X-rays 2 diffracted from a sample S are directly focused (see FIG. 10) to the extent that the monochromator 60 does not interfere with the X-ray detector 20.

Figure 3B:
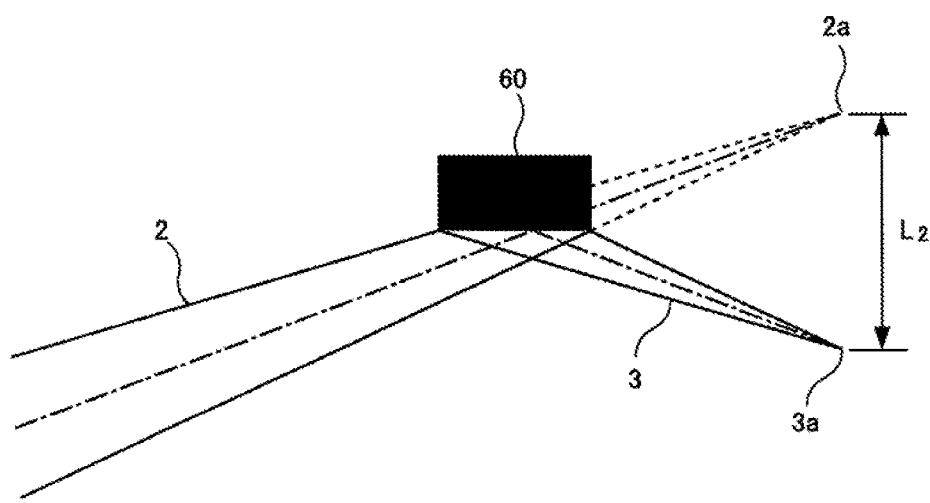

FIGS. 3A and 3B are diagrams showing the relationship between the installation/removal of the monochromator and the positional variation of the focal point at which the focusing X-rays focus.

In a state where the monochromator 60 is removed (that is, the X-ray optical system shown in FIG. 10), the focusing X-rays 2 diffracted from the sample S focus at a first focal point 2a shown in FIG. 3A. On the other hand, in a state where the monochromator 60 is arranged on the optical path of the focusing X-rays 2 (that is, the X-ray optical system shown in FIG. 1), the focusing X-rays 2 diffracted from the sample S are incident to the surface of the monochromator 60, and monochromated focusing X-rays 3 having a specific wavelength are reflected from the monochromator 60. These focusing X-rays 3 reflected from the monochromator 60 focus at a second focal point 3a shown in FIG. 3A.

In the optical system shown in FIG. 3A, the monochromator 60 is arranged in proximity to the first focal point 2a, so that the second focal point 3a of the focusing X-rays 3 reflected from the monochromator 60 is approximate to the first focal point 2a and thus the distance $L_1$ between the focal points 2a and 3a is short.

On the other hand, as the monochromator 60 is separated from the first focal point 2a, the second focal point 3a of the focusing X-rays 3 reflected from the monochromator 60 is farther away from the first focal point 2a, and thus the distance $L_2$ between the focal points 2a and 3a is longer as shown in FIG. 3B.

Considering the relationship between the locating position of the monochromator 60 and the positional variation of the focal point 3a as described above, the X-ray diffractometer of this embodiment is arranged in proximity to the first focal point 2a at which the focusing X-rays 2 diffracted from the sample S are focused as they are.

Accordingly, the distance between the first focal point 2a and the second focal point 3a can be shortened. As a result, a configuration which is adaptable to both of the X-ray optical system of FIG. 10 and the X-ray optical system of FIG. 1 can be implemented while the X-ray detector 20 is fixed as described later. When the monochromator 60 is arranged in proximity to the first focal point 2a, the incident area of the focusing X-rays 2 to the monochromator 60 is reduced, so that the monochromator 60 can be miniaturized (see FIG. 3A).

A two-dimensional X-ray detector capable of two-dimensionally detecting X-rays incident to the X-ray detection face 21 is used as the X-ray detector 20. The X-ray diffractometer is configured that the X-ray detection face 21 of a single X-ray detector 20 is enabled to detect the focusing X-rays 2 diffracted from the sample S in the X-ray optical system from which the monochromator 60 is removed (the X-ray optical system of FIG. 10) and also detect the focusing X-rays 3 reflected from the monochromator 60 in the X-ray optical system having the monochromator 60 arranged therein (the X-ray optical system of FIG. 1).

As described above, the X-ray diffractometer is configured to be adaptable to both the X-ray optical system of FIG. 10 and the X-ray optical system of FIG. 1 while the single X-ray detector 20 is fixed, which facilitates switching between the optical systems.

Figure 4:
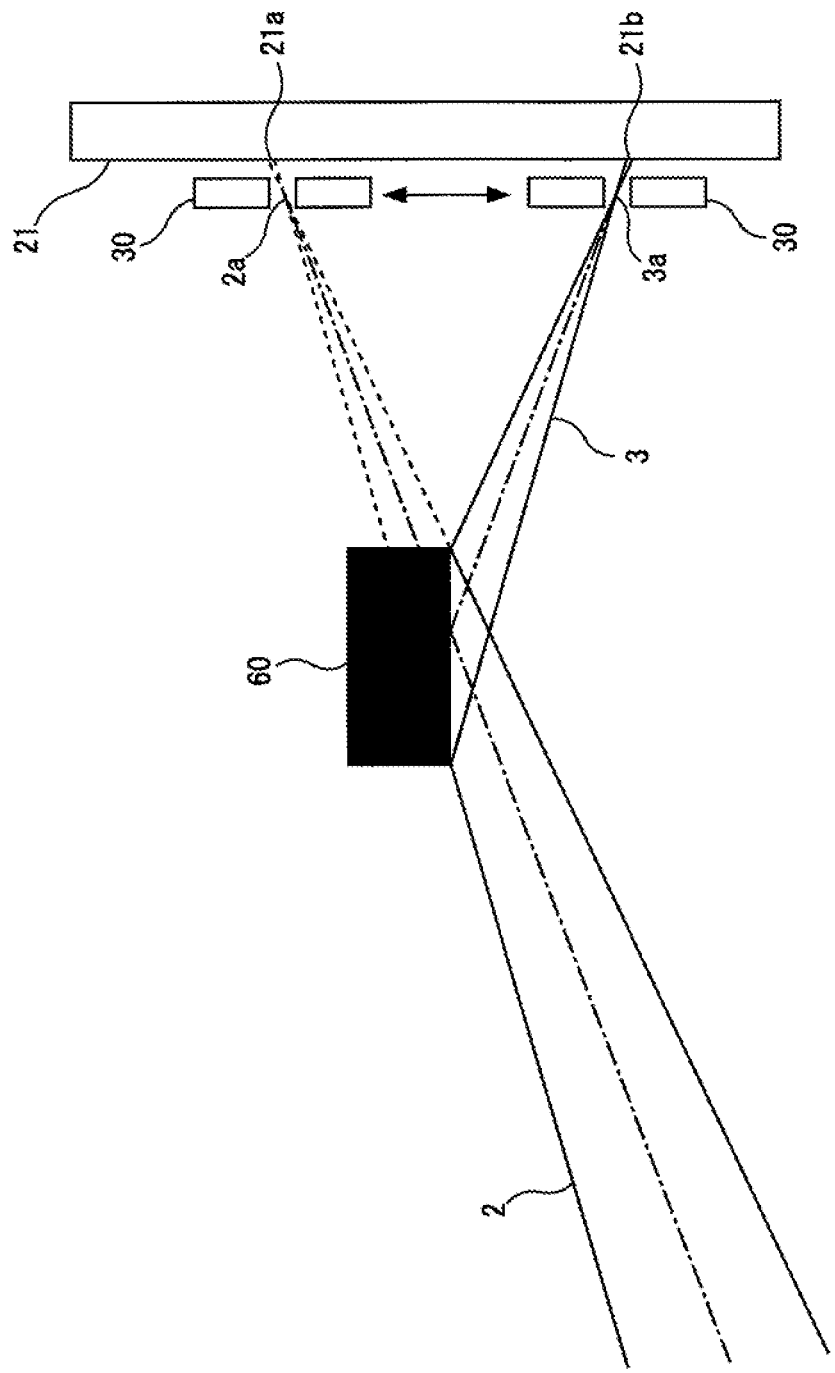
FIG. 4 is a schematic diagram showing the movement of a receiving position of focusing X-rays on the X-ray detection face of an X-ray detector and the positional change of a receiving slit.

FIG. 4 is a schematic diagram showing the movement of the receiving position for focusing X-rays on the X-ray detection face of the X-ray detector and the positional change of the receiving slit.

The X-ray detection face 21 of the X-ray detector 20 is arranged at (or proximately behind) the focal point 2a or 3a of the focusing X-rays 2 or 3. This arrangement relationship will be described in detail later.

As shown in FIG. 4, the focusing X-rays 2 diffracted from the sample S are incident to a first receiving position 21a on the X-ray detection face 21 of the X-ray detector 20 in the X-ray optical system in which the monochromator 60 is removed from the optical path of the focusing X-rays 2 (the X-ray optical system of FIG. 10), whereas the focusing X-rays 3 reflected from the monochromator 60 are incident to a second receiving position 21b on the X-ray detection face 21 of the X-ray detector 20 in the X-ray optical system in which the monochromator 60 is arranged on the optical path of the focusing X-rays 2 (the X-ray optical system of FIG. 1).

Accordingly, the position of the receiving slit 30 arranged in front of the X-ray detection face 21 of the X-ray detector 20 is required to be changed according to the installation/removal of the monochromator 60. That is, for the X-ray optical system in which the monochromator 60 is removed from the optical path of the focusing X-rays 2 (the X-ray optical system of FIG. 10), the receiving slit 30 is arranged in front of the first receiving position 21a to pass the focusing X-rays 2 diffracted from the sample S therethrough. On the other hand, for the X-ray optical system in which the monochromator 60 is arranged on the optical path of the focusing X-rays 2 (the X-ray optical system of FIG. 1), the receiving slit 30 is arranged in front of the second receiving position 21b to pass the focusing X-rays 3 reflected from the monochromator 60 therethrough.

The positional change of the receiving slit 30 may be performed manually or automatically. When the receiving slit 30 is automatically positionally changed, a driving mechanism for the receiving slit 30 may be installed to move the receiving slit 30 with driving force from the driving mechanism.

As the X-ray detector 20 is preferably used a multifunctional two-dimensional X-ray detector that has a two-dimensional X-ray detection function capable of two-dimensionally detecting X-rays incident to the X-ray detection face 21, a one-dimensional X-ray detection function capable of one-dimensionally detecting X-rays incident to the X-ray detection face 21 and a zero-dimensional X-ray detection function capable of zero-dimensionally detecting X-rays incident to the X-ray detection face 21, and is configured to switch these functions.

As described above, the zero-dimensional detection of X-rays means that only the intensity of X-rays is detected, the one-dimensional detection of X-rays means that the intensity of X-rays and one-dimensional position information are detected, and the two-dimensional detection of X-rays means that the intensity of X-rays and two-dimensional position information are detected.

Figure 5A:
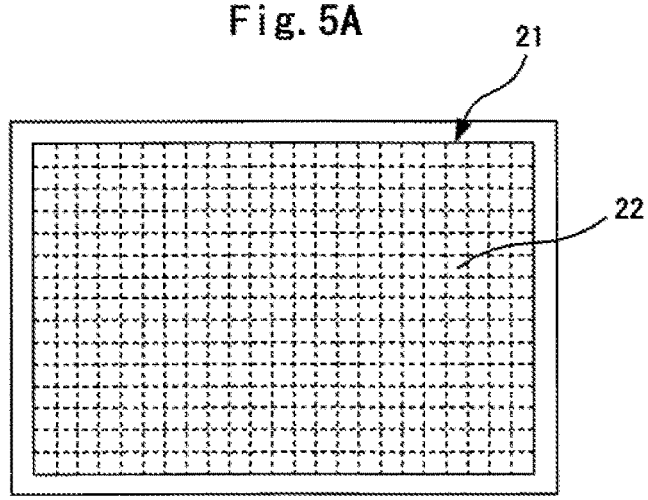
FIGS. 5A, 5B and 5C are schematic diagrams showing the principle of a multifunctional two-dimensional X-ray detector.
Figure 5B:
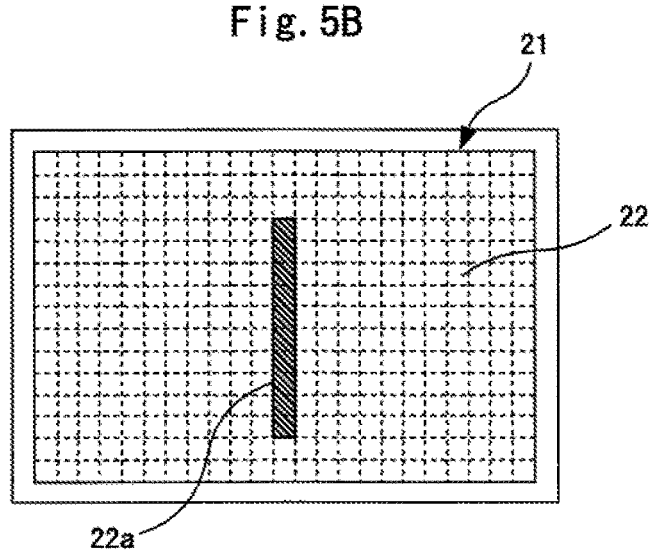
Figure 5C:
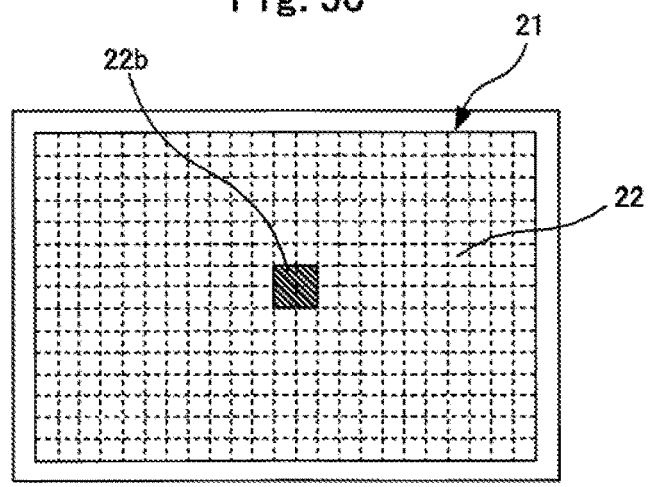

FIGS. 5A, 5B and 5C are schematic diagrams showing the principle of this type of multifunctional two-dimensional X-ray detector.

In the two-dimensional X-ray detector 20, one rectangular X-ray detection face 21 is formed by plural detection elements 22 arranged two-dimensionally as shown in FIG. 5A. The respective detection elements 22 are arranged in a lattice form in two directions which are orthogonal to each other (in a lateral direction and a longitudinal direction in FIG. 5A). Each detection element 22 detects the intensity of X-rays incident thereto. Specifically, when X-rays are incident to a detection element 22, this detection element 22 generates a detection signal (electrical signal or the like) proportional to the intensity of the incident X-rays. Therefore, when X-rays are detected by the two-dimensional X-ray detector 20, detection signals whose number is equal to the number of the detection elements 22 forming the X-ray detection face 21 can be obtained.

By changing the range in which the detection elements 22 constituting the X-ray detection face 21 are used, any one of the two-dimensional X-ray detection function, the one-dimensional X-ray detection function and the zero-dimensional X-ray detection function can be selected, whereby the X-ray detection mode can be switched.

That is, when the respective detection elements 22 arranged over the whole X-ray detection face 21 are used as shown in FIG. 5A, the function as the two-dimensional X-ray detector capable of two-dimensionally detecting X-rays incident to the X-ray detection face 21 can be exercised. Furthermore, when only plural detection elements 22a arranged on a line segment are used as shown in FIG. 5B, the function as the one-dimensional X-ray detector capable of one-dimensionally detecting X-rays incident to the X-ray detection face 21 can be exercised. Still furthermore, when only one of the detection elements 22b or plural lumped detection elements 22b arranged on the X-ray detection face 21 are used as shown in FIG. 5C, the function as the zero-dimensional X-ray detector capable of zero-dimensionally detecting X-rays incident to the X-ray detection face 21 can be exercised.

Each of the two-dimensional X-ray detection, the one-dimensional X-ray detection and the zero-dimensional X-ray detection in the X-ray optical system from which the monochromator 60 is removed (the X-ray optical system of FIG. 10), and the two-dimensional X-ray detection, the one-dimensional X-ray detection and the zero-dimensional X-ray detection in the X-ray optical system in which the monochromator 60 is arranged on the optical path of focusing X-rays 2 (the X-ray optical system of FIG. 1) can be arbitrarily selected to perform X-ray diffraction measurements by using the multifunctional two-dimensional X-ray detector as described above. Therefore, the degree of freedom of measurements can be remarkably increased.

Generally, a manner of removing the monochromator 60 from the optical path of focusing X-rays 2 to make the focusing X-rays 2 having a large X-ray intensity incident to the X-ray detector 20 is adopted in the case of the two-dimensional X-ray detection or the one-dimensional X-ray detection. On the other hand, a manner of arranging the monochromator 60 on the optical path of the focusing X-rays 2 to detect the focusing X-rays 2 with high detection precision is adopted in the case of the zero-dimensional X-ray detection.

Figure 6A:
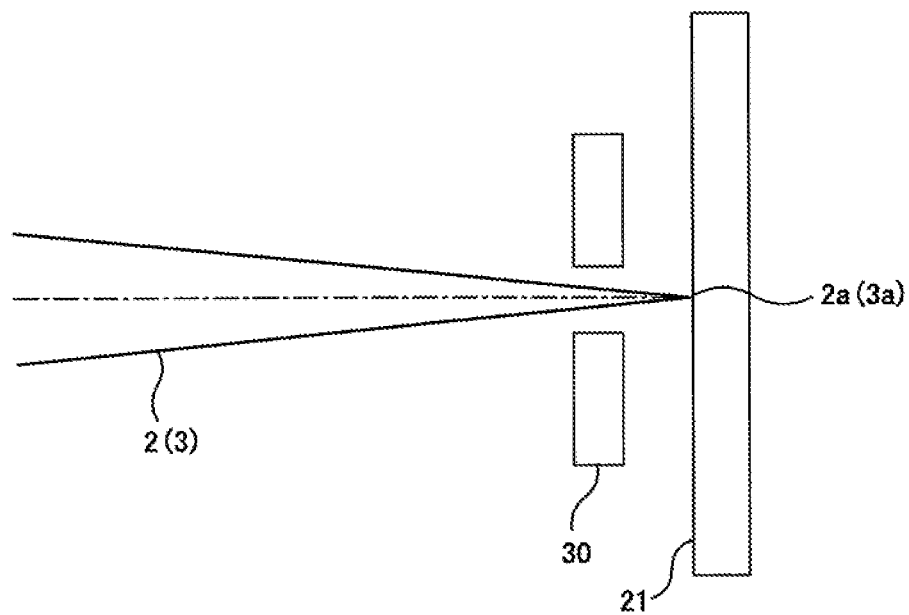
FIGS. 6A and 6B are schematic diagrams showing the arrangement relationship of the X-ray detection face of the X-ray detector and the receiving slit with respect to the focal point of focusing X-rays as a detection target.
Figure 6B:
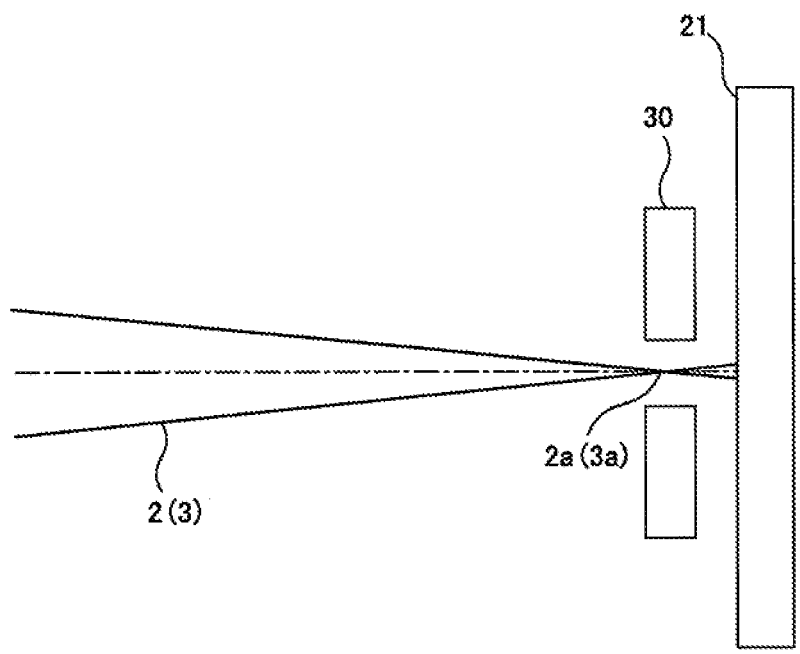
Figure 9A:
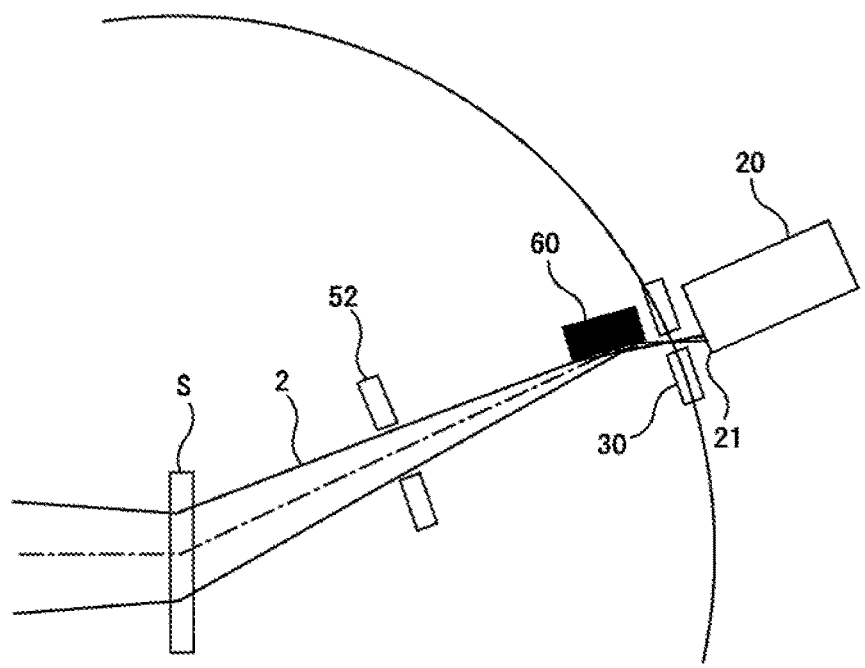
FIGS. 9A and 9B are schematic diagrams showing an application example when the present invention is applied to a transmission type X-ray optical system.
Figure 9B:
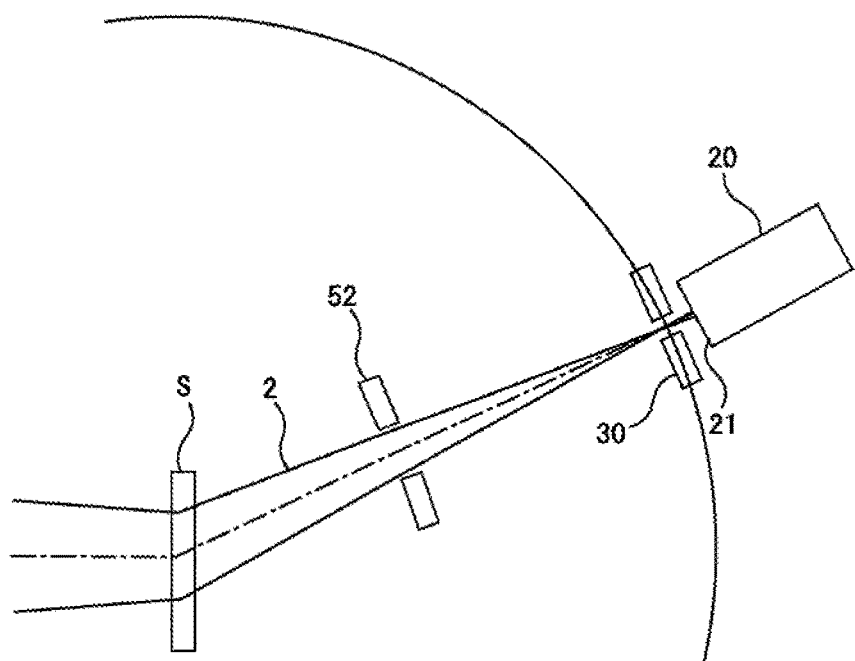
Figure 11:
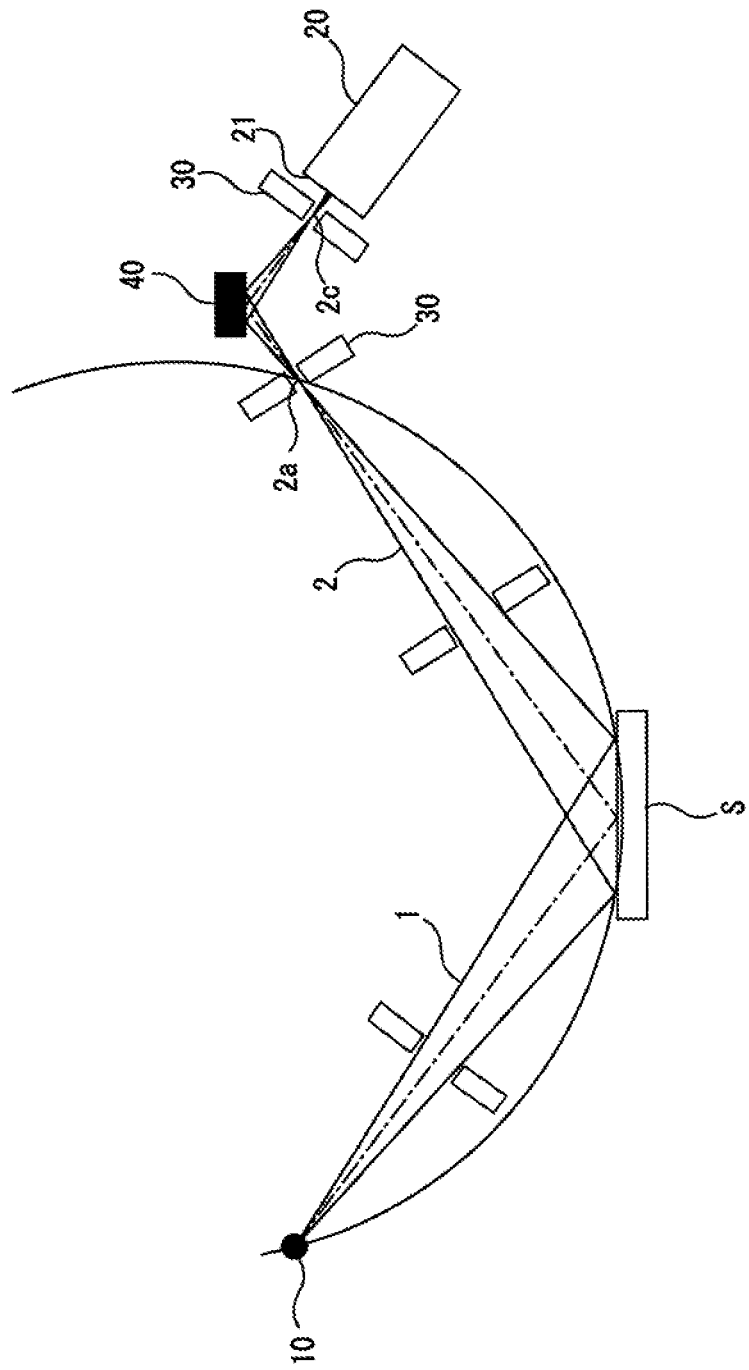
FIG. 11 is a schematic diagram showing an exemplary arrangement of an X-ray optical system in a conventional X-ray diffractometer in which a monochromator is arranged.

In the case of the two-dimensional X-ray detection or the one-dimensional X-ray detection, it is preferable that the X-ray detection face 21 of the X-ray detector 20 is arranged at the focal point 2a (or 3a) of the focusing X-rays 2 (or 3) as a detection target as shown in FIG. 6A. On the other hand, in the case of the zero-dimensional X-ray detection, it is preferable that the receiving slit 30 is arranged at the focal point 2a (or 3a) of the focusing X-rays 2 (or 3) as a detection target, and the X-ray detection face 21 of the X-ray detector 20 is arranged to be proximate to and behind the receiving slit 30 as shown in FIG. 6B.

Second Embodiment

Next, an X-ray diffractometer according to a second embodiment of the present invention will be described with reference to FIG. 7.

FIG. 7 is a schematic diagram showing a main part of the X-ray diffractometer according to the second embodiment.

The whole structure of the X-ray diffractometer according to this embodiment is the same as the apparatus of the first embodiment described above.

In this embodiment, the X-ray detector 20 is configured to be moved integrally with the receiving slit 30.

That is, the receiving slit 30 and a detection area confronting the receiving slit 30 on the X-ray detection face 21 of the X-ray detector 20 are moved to any of the following positions. First, in the case of the X-ray optical system from which the monochromator 60 is removed (the X-ray optical system of FIG. 10), they are arranged on the optical path of the focusing X-rays 2 diffracted from the sample S. On the other hand, in the case of the X-ray optical system in which the monochromator 60 is arranged (the X-ray optical system of FIG. 1), they are arranged on the optical path of the focusing X-rays 3 which are diffracted from the sample S and reflected from the monochromator 60.

In the X-ray diffractometer according to this embodiment, the X-ray detector 20 is moved, and thus it is less necessary to arrange the monochromator 60 in proximity to the focal point 2a (see FIG. 10) at which the focusing X-rays 2 diffracted from the sample S are directly focused compared with the first embodiment described above. However, in order to suppress the movement amount of the X-ray detector 20 to the minimum level, it is still preferable to arrange the monochromator 60 in proximity to the focal point 2a (see FIG. 10) at which the focusing X-rays 2 diffracted from the sample S are directly focused.

For example, a detection unit moving device (9) disclosed in the Patent Document 3 is applicable as a mechanism for integrally moving the X-ray detector 20 and the receiving slit 30.

In this embodiment, the X-ray detector 20 and the receiving slit 30 are moved integrally with each other. However, the present invention is not limited to this configuration, and the X-ray detector 20 and the receiving slit 30 may be configured to be moved separately from each other.

Third Embodiment

Next, an X-ray diffractometer according to a third embodiment of the present invention will be described with reference to FIG. 8.

FIG. 8 is a schematic diagram showing a main part of the X-ray diffractometer according to the third embodiment.

The whole structure of the X-ray diffractometer according to this embodiment is the same as the apparatus of the first embodiment described previously.

This embodiment uses a two-dimensional X-ray detector 20 having a function of freely changing the X-ray detection area. The function of freely changing the X-ray detection area in the two-dimensional X-ray detector 20 constitutes a unit that adjusts the measurement resolution of the X-ray detector 20. Accordingly, the receiving slit 30 is removed from the X-ray diffractometer of this embodiment.

With respect to the X-ray detection face 21 of the two-dimensional X-ray detector 20, one rectangular X-ray detection face 21 is formed by plural detection elements 22 which are two-dimensionally arranged as shown in FIG. 5A. The respective detection elements 22 are arranged in a lattice form in two directions which are orthogonal to each other (in lateral and longitudinal directions in the figure) to detect the intensities of X-rays incident thereto.

In this embodiment, detection elements 22 to be used for detection of X-rays are selected from the plural detection elements 22 forming the X-ray detection face 21, whereby an arbitrary X-ray detection area can be formed on the X-ray detection face 21.

That is, as shown in FIG. 8, in the case of the X-ray optical system from which the monochromator 60 is removed (the X-ray optical system of FIG. 10), the X-ray detector 20 forms a first X-ray detection area by using only detection elements 22c in an area to which the focusing X-rays 2 diffracted from the sample S are incident, and in the case of the X-ray optical system in which the monochromator 60 is arranged (the X-ray optical system of FIG. 1), the X-ray detector 20 forms a second X-ray detection area by using only detection elements 22d in an area to which the focusing X-rays 3 diffracted from the sample S and reflected from the monochromator 60 are incident. The detection elements 22 in areas other than the above areas are not used.

With this configuration, the detection elements 22c or 22d which form the first X-ray detection area or the second X-ray detection area also serve as a receiving slit 30, and thus the receiving slit 30 can be omitted.

For example, the configuration of "virtual mask" disclosed in Japanese Patent Application No. 2013-243506 filed previously by the applicant of this application may be used as the configuration that the X-ray detection area of the two-dimensional X-ray detector 20 is freely changeable.

It is needless to say that the present invention is not limited to the above embodiments, and various modifications or applications may be performed.

For example, the fundamental X-ray optical system is not limited to the configurations shown in FIGS. 10 and 1. For example, the present invention is applicable to a transmission type X-ray optical system for irradiating a sample S with focusing X-rays 2 and transmitting therethrough X-rays diffracted in the sample S so that the X-rays focus on one point as in the above embodiments.

Furthermore, the two-dimensional X-ray detector is used in the above embodiments. However, a dedicated one-dimensional X-ray detector or zero-dimensional X-ray detector may be used as occasion demands.

The above embodiments are configured so that the monochromator 60 can be freely installed/removed in/from the optical path of the focusing X-rays 2. However, the embodiments may be configured so that the monochromator 60 can be evacuated from the optical path of the focusing X-rays 2 by moving the monochromator 60 on the apparatus without removing the monochromator 60 from the apparatus.

Figure 12:
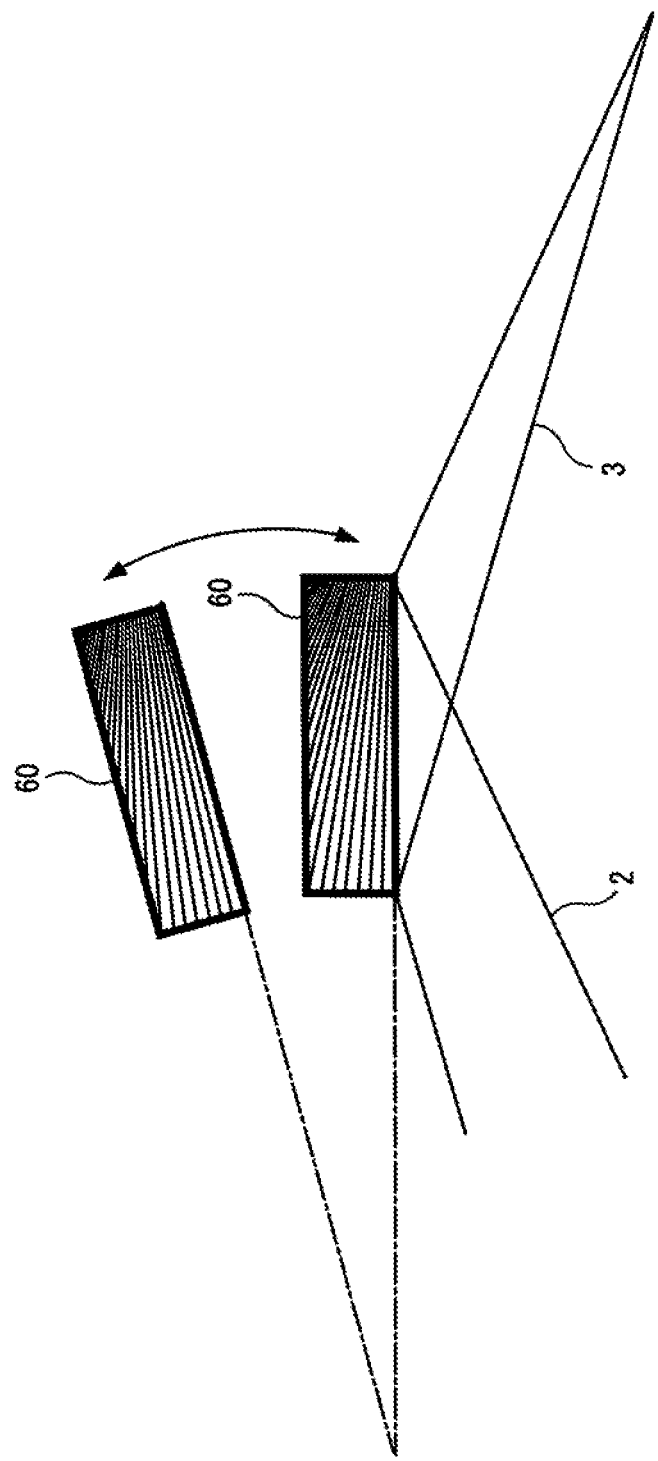
FIG. 12 is a schematic diagram showing a mechanism for evacuating the monochromator from the optical path of focusing X-rays.
Figure 13:
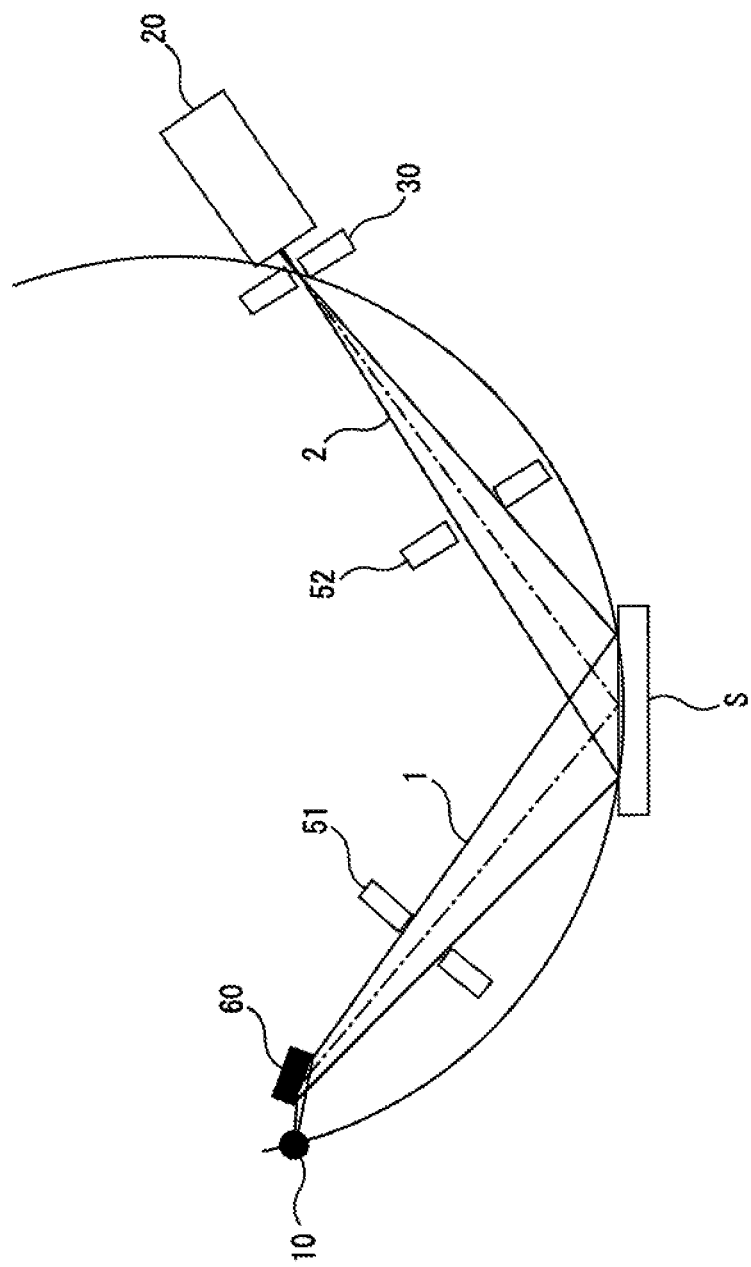
FIG. 13 is a schematic diagram showing an application example when a monochromator is arranged on the optical path of divergent X-rays which are radially emitted from an X-ray source and applied to a sample.

For example, as shown in FIG. 12, a mechanism for turning the monochromator 60 is provided, and the monochromator is arranged on the optical path of focusing X-rays 2 or evacuated from the optical path of the focusing X-rays 2 by the turning operation.

Furthermore, as an application of the present invention, the X-ray diffractometer may be configured so that the monochromator 60 is arranged on the optical path of divergent X-rays which are radially emitted from the X-ray source and applied to the sample, and the divergent X-rays incident to the sample are monochromated by the monochromator 60. The monochromator 60 is arranged in proximity to the X-ray source 10. In this configuration, the reflection type monochromator used in the embodiments of the present invention may be applied as the monochromator 60.

The invention claimed is:

1. An X-ray diffractometer comprising:
an X-ray source for irradiating a sample with X-rays;
a reflection type monochromator for receiving diffracted focused X-rays and reflecting only focused X-rays having a specific wavelength based on a Bragg's condition;
an X-ray detector for detecting monochromated focused X-rays; and
a unit that adjusts measurement resolution of the X-ray detector, wherein the monochromator is arranged on an X-ray optical path between a focal point at which the diffracted focused X-rays from the sample are directly focused and the sample.

2. The X-ray diffractometer according to claim 1, wherein the monochromator comprises a multilayer mirror having an internal interplanar spacing that varies continuously from one end to the other end.

3. The X-ray diffractometer according to claim 2, wherein the monochromator has an incident face for the focusing X-rays, the incident face being configured to be a flat surface.

4. The X-ray diffractometer according to claim 2, wherein the interplanar spacing in the multilayer mirror is adjusted so that a interplanar spacing $d_1$ in a depth direction at a site to which the focusing X-rays are incident at an incident angle $\theta_1$ and a interplanar spacing $d_2$ in the depth direction at a site to which the focusing X-rays are incident at an incident angle $\theta_2$ satisfy the following equation based on the Bragg's condition: $2d_1 \times \sin\theta_1 = 2d_2 \times \sin\theta_2 = n\lambda$ wherein $\lambda$ represents the wavelength of the diffracted X-rays, and n represents an integer.

5. The X-ray diffractometer according to claim 1, wherein the monochromator is arranged in proximity to a focal point at which the diffracted focused X-rays are directly focused to the extent that the monochromator does not interfere with the X-ray detector.

6. The X-ray diffractometer according to claim 5, wherein the unit that adjusts the measurement resolution of the X-ray detector comprises a receiving slit arranged in front of an X-ray detection face in the X-ray detector.

7. The X-ray diffractometer according to claim 6, wherein the X-ray detector comprises a two-dimensional X-ray detector that is adapted to two-dimensionally detect X-rays incident to the X-ray detection face.

8. The X-ray diffractometer according to claim 6, wherein the monochromator is removable from the optical path of the diffracted focused X-rays;
the X-ray detection face of the X-ray detector has an area that allows detection of the diffracted focused X-rays in an X-ray optical system in which the monochromator is removed from the optical path of the focusing X-rays and detection of the diffracted focused X-rays and focusing X-rays reflected from the monochromator in an X-ray optical system in which the monochromator is arranged on the optical path of the focusing X-rays; and
the receiving slit is configured to be freely positionally changeable between a position through which the diffracted focused X-rays pass in the X-ray optical system in which the monochromator is removed from the optical path of the focusing X-rays, and a position through which the diffracted focused X-rays and focusing X-rays reflected from the monochromator pass in the X-ray optical system in which the monochromator is arranged on the optical path of the focusing X-rays.

9. The X-ray diffractometer according to claim 6, wherein the monochromator is removable from the optical path of the diffracted focused X-rays;
the receiving slit is configured to be freely positionally changeable between a position through which the diffracted focused X-rays pass in an X-ray optical system in which the monochromator is removed from the optical path of the focusing X-rays, and a position through which the diffracted focused X-rays and focusing X-rays reflected from the monochromator pass in an X-ray optical system in which the monochromator is arranged on the optical path of the focusing X-rays; and
the X-ray detector is configured to be freely positionally changeable between a detection position of the diffracted focused X-rays and focusing X-rays passing through the receiving slit in the X-ray optical system in which the monochromator is removed from the optical path of the focusing X-rays, and a detection position of the diffracted focused X-rays, focusing X-rays reflected from the monochromator and passing through the receiving slit in the X-ray optical system in which the monochromator is arranged on the optical path of the focusing X-rays.

10. The X-ray diffractometer according to claim 5, wherein the monochromator is removable from the optical path of the diffracted focused X-rays;
the X-ray detector comprises a two-dimensional X-ray detector that is adaptable to two-dimensionally detect X-rays incident to the X-ray detection face;
the X-ray detection face of the X-ray detector has an area that allows detection of diffracted focused X-rays in an X-ray optical system in which the monochromator is removed from the optical path of the focusing X-rays and detection of diffracted focused X-rays and focusing X-rays reflected from the monochromator in an X-ray optical system in which the monochromator is arranged on the optical path of the focusing X-rays;

the X-ray detector has a function of freely changing an X-ray detection area between a first X-ray detection area for detecting the diffracted focused X-rays in the X-ray optical system in which the monochromator is removed from the optical path of the focusing X-rays, and a second X-ray detection area for detecting the diffracted focused X-rays and focusing X-rays reflected from the monochromator in the X-ray optical system in which the monochromator is arranged on the optical path of the focusing X-rays; and the function of freely changing the X-ray detection area in the X-ray detector constitutes a unit that adjusts measurement resolution of the X-ray detector.

11. The X-ray diffractometer according to claim 7, wherein the two-dimensional X-ray detector is configured to have a two-dimensional X-ray detection function capable of two-dimensionally detecting X-rays incident to the X-ray detection face, a one-dimensional X-ray detection function capable of one-dimensionally detecting X-rays incident to the X-ray detection face and a zero-dimensional X-ray detection function capable of zero-dimensionally detecting X-rays incident to the X-ray detection face, the two-dimensional X-ray detection function, the one-dimensional X-ray detection function and the zero-dimensional X-ray detection function being switchable to one another.

12. The X-ray diffractometer according to claim 10, wherein the two-dimensional X-ray detector is configured to have a two-dimensional X-ray detection function capable of two-dimensionally detecting X-rays incident to the X-ray detection face, a one-dimensional X-ray detection function capable of one-dimensionally detecting X-rays incident to the X-ray detection face and a zero-dimensional X-ray detection function capable of zero-dimensionally detecting X-rays incident to the X-ray detection face, the two-dimensional X-ray detection function, the one-dimensional X-ray detection function and the zero-dimensional X-ray detection function being switchable to one another.

* * * * *